United States Patent [19]

Lipscher et al.

[11] Patent Number: 5,785,051
[45] Date of Patent: Jul. 28, 1998

[54] SIGNAL GENERATING ENDOTRACHEAL TUBE APPARATUS

[75] Inventors: Randolph B. Lipscher; Jack G. Mottley. both of Rochester. N.Y.

[73] Assignee: University of Rochester. Rochester. N.Y.

[21] Appl. No.: 667,674

[22] Filed: Jun. 21, 1996

[51] Int. Cl.$^6$ ............................................. A61M 16/00
[52] U.S. Cl. ........................... 128/207.15; 128/207.14; 128/200.26
[58] Field of Search .................. 128/207.14, 207.15, 128/200.26

[56] References Cited

U.S. PATENT DOCUMENTS

| | | | |
|---|---|---|---|
| 4,466,443 | 8/1984 | Utsugi | 128/660 |
| 4,633,882 | 1/1987 | Matsuo et al. | 128/660 |
| 4,671,295 | 6/1987 | Abrams et al. | 128/663 |
| 4,722,347 | 2/1988 | Abrams et al. | 128/663 |
| 4,886,059 | 12/1989 | Weber | 128/207.15 |
| 5,076,268 | 12/1991 | Weber | 128/207.15 |
| 5,203,777 | 4/1993 | Lee | 128/658 |
| 5,279,610 | 1/1994 | Park et al. | 606/108 |
| 5,425,370 | 6/1995 | Vilkomerson | 128/662.06 |
| 5,437,290 | 8/1995 | Bolger et al. | 128/898 |
| 5,546,949 | 8/1996 | Frazin et al. | 128/662.06 |

OTHER PUBLICATIONS

Hayden et al., "Colorimetric End-tidal $CO_2$ Detector for Verification of Endotracheal Tube Placement in Out-of-Hospital Cardiac Arrest," *Academic Emergency Medicine*, 2(6):499–502 (1995).

Marley et al., "Evaluation of a Prototype Esophageal Detection Device," *Academic Emergency Medicine*, 2(6):503–507 (1995).

McCormick et al., "Pediatric Tracheal Intubation System that may Reduce X–ray Use; Preclinical Assessment," *IEEE/Eighth Annual Conference of the Engineering in Medicine and Biology Society*, pp. 140–142 (1986).

Mansfield et al., "An Acoustical Guidance and Position Monitoring System for Endotracheal Tubes," *IEEE Transactions on Biomedical Engineering*, 40(12):1330–1334 (1993).

Rao et al., "Model of a New Generation of Tracheostomy and Endotracheal Tubes. A Preliminary Study of Sensors to Monitor Obstruction," *Ann. Otol. Rhinol. Laryngol. (USA)*, 98/2:157–159 (1989) Abstract.

Maltais et al., "Respiratory Mechanics in Status Asthmaticus: Effects of Inhalational Anesthesia," *Chest*, 106(5):1401–1406 (Abstract).

*Primary Examiner*—Aaron J. Lewis
*Attorney, Agent, or Firm*—Nixon. Hargrave. Devans & Doyle LLP

[57] ABSTRACT

The present invention is directed to an endotracheal apparatus for providing reliable airway management in a patient. A flexible tube extends from the patient's oral or nasal cavity to a distal end within the trachea. A first ultrasound transducer means connected to the tube near its distal end is in intimate contact with the forward inner wall of the patient's trachea at substantially its midpoint. A second ultrasound transducer means is disposed in intimate contact with the forward outer skin surface of the patient's neck. Either the first or the second transducer means can be a transmitter of an ultrasound signal provided by ultrasound transducer excitation means, to which it is electrically connected. The other transducer means serves as a receiver, which is connected to ultrasound detector means situated externally to the patient. Also in accordance with the invention, a process for monitoring the position of an endotracheal tube inserted in a patient utilizes an apparatus that comprises first transducer means disposed within the trachea of the patient and second transducer means disposed on the outer skin surface of the patient's neck.

27 Claims, 4 Drawing Sheets

SIGNAL GENERATING ENDOTRACHEAL TUBE APPARATUS

FIELD OF THE INVENTION

This invention relates to airway management devices for use in medical emergencies and more particularly to an endotracheal tube apparatus that generates a signal to ensure proper placement of the tube in a patient's trachea.

BACKGROUND OF THE INVENTION

Airway management is fundamental to emergency medicine. In resuscitation it is the first priority. Complete airway obstruction leads to cardiac arrest within 4 minutes. Irreversible central nervous system damage occurs within 3 to 5 minutes of ventilatory compromise. Definitive airway control is provided by endotracheal intubation, which involves introducing a balloon tipped, large gauge, catheter past the vocal cords and securing the catheter by expanding the balloon. In an adult, the tip of a properly positioned endotracheal tube is located about 5 to 7 cm into the trachea, approximately its midpoint.

Endotracheal tubes are now routinely placed in the operating theatre by anesthesiologists, in the emergency department by emergency department physicians, in the ICU by ICU physicians, and in the pre-hospital setting by paramedics skilled in critical care interventions. Despite the ubiquitous and routine use of endotracheal tubes to oxygenate and ventilate patients, misplacement of the endotracheal tube remains a serious problem, with life threatening consequences. Significant morbidity and mortality may occur as a consequence of: placement of the endotracheal tube into the esophagus; placement or movement of the tube into the right main bronchus; or dislodgement of the tube as a result of patient movement, causing its repositioning in either the pharynx or bronchus.

A review of various anesthetic-related morbidity and mortality statistics indicates that unrecognized esophageal intubation remains a problem, even among anesthesiologists. An analysis of anesthetic accidents in the United Kingdom from 1970 to 1978, for example, revealed that nearly half the cases resulting in death or cerebral damage were due to inadvertent placement of the endotracheal tube into the esophagus. Another review of anesthesia-related medical liability claims in the United Kingdom from 1977 to 1982 listed esophageal intubation as a main cause of accidents leading to death or neurologic damage. A review of malpractice claims brought against Washington State anesthesiologists from 1971–1982 concluded that esophageal intubation figured prominently among complications resulting in cardiac arrest, brain damage, and death.

Malpositioning of the endotracheal tube within the airway after intubation can result in serious complications, particularly in the critically ill patient requiring emergent intubation. Endobronchial placement of the endotracheal tube leads to atelectasis of the non-ventilated lung and to decreased oxygenation. The lung that is ventilated may become hyperventilated, causing barotrauma and hypotension. If respiratory function of an endobronchially intubated patient is already impaired by additional damage (lung contusion, hemothorax, pneumothorax, shock, etc.), systemic hypoxemia rapidly develops and cannot be satisfactory compensated by higher concentrations of inspiratory oxygen. Furthermore, endobronchially intubated patients with chest injuries, aspiration, or both are at high risk of acute post-traumatic respiratory insufficiency. In the presence of brain injury and or shock, hypoxemia, hypercapnia, hypotension, and rising intracranial pressure can lead to reduction of intracerebral compliance and, due to resulting ischemia, to further secondary brain damage.

In a retrospective study of 100 emergency patients, Bissinger et al ("Unrecognized Endobronchial Intubation in Emergency Patients," *Annals of Emergency Medicine*, 1989, Vol. 18, No. 8, pp. 853–855) concluded that: "inadvertent endobronchial intubation was not recognized by the physician or the admitting anesthesiologist in 7 percent of the reviewed cases, and endotracheal malpositioning of the tip near the carina (2 cm or less) occurred in another 13 percent." Furthermore, Bissinger stated that "Evaluation of the depth of tube insertion with the aid of common clinical techniques is particularly unreliable in the case of thoracic trauma, aspiration, or previously existing pulmonary disease."

Placement of the endotracheal tube too high in the airway can increase the likelihood of accidental extubation, with resultant hypoxemia and hypoventilation. Appropriate endotracheal tube position has been determined to mean that the tip of the tube is located substantially at the midpoint of the trachea. This is generally accepted as between 2 and 6 cm above the carina, with the patient's head in a neutral position. Since marked alterations in the endotracheal tube position occur with changes in head position, the location of the endotracheal tube becomes very significant after emergent intubation. Flexion of the neck from the neutral position can result in the tip of the endotracheal tube moving as much as 3 cm closer to the carina, while extension can displace the tube up to the 5 cm farther than the carina. Lateral movement of the neck can cause the tip of the endotracheal tube to move 2 cm from the carina. Such changes of head position are typical with normal patient movement in the ICU, emergency department, and in the prehospital setting.

Thus, emergent endotracheal intubation results in significant occurrence of malpositioned endotracheal tubes that are undetected by clinical evaluation. Malpositioning is not detected by routine clinical assessment, but only by chest radiograph. Patients may be extubated during movement to a hospital, and the extubation may well not be discovered until the patient arrives at the hospital. This leads to potentially long periods of anoxia and potentially devastating sequela.

Numerous methods and devices are available for the determination of endotracheal tube location, i.e., esophageal vs. tracheal intubation. Direct visualization of the vocal cords and watching the tube pass into the trachea is considered by many as the "gold standard" of correct tube placement and remains one of the most reliable signs. Unfortunately, this is impossible to achieve in certain patients. Furthermore, even after visualization of the cords and tube placement, the tube may be inadvertently withdrawn from the trachea prior to or during securing of the tube, or with positioning of the patient in the lateral or prone position. Additionally, flexion or extension of the neck can change tube position as much as 5 cm, resulting in inadvertent extubation.

Another commonly relied upon measure is observation of symmetric bilateral movements of the chest wall during ventilation. However, conditions in which ventilation is more than usually dependent on diaphragmatic movement make assessment of proper tube position by chest expansion difficult. In an obese patient, or in a patient with large breasts, a barrel chest from lung disease, or other conditions that result in a rigid chest wall, chest movement can be difficult to evaluate. More importantly, movement of the chest wall simulating ventilation of the lungs can be seen with the esophageally positioned tube.

The presence of bilateral breath sounds upon apical and/or midaxillary auscultation of the lungs would seem to provide strong reassurance of proper tube position. However, even experienced clinicians have mistaken breath sounds as normal with esophageal ventilation. Air passing through the esophagus may resemble course or tubular breath sounds. Furthermore, with mechanical or hand ventilation, gas flows tend to be faster, tidal volumes larger, and distribution different from what is observed with spontaneous respiration. Breath sounds are more predominantly bronchial and may differ in quality, depending on whether the chest is auscultated over the midline or laterally, which may explain why sounds produced by air movement through an esophageal tube may be mistaken as breath sounds.

Chest radiography to verify proper tube position is time consuming and expensive, yet still not fail-safe. It is common practice to obtain chest radiographs in the ICU to confirm the position of the tracheal tube. This procedure is considered undesirable because of the potentially excessive irradiation during ventilatory support. A further disadvantage of current radiographic procedures is that they do not provide real time information about tube position because of the interval required to set up the X-ray apparatus and to develop and return the film to medical personnel. Finally, X-ray methods are expensive and entail the risk of inadvertent exposure to medical personnel.

Lung ventilation has been monitored by intraoperative use of a video stethoscope device that includes a small plastic electrocardiographic electrode casing fitted with a microphone and placed on the skin overlying each hemithorax. By displaying the sound from each microphone on an oscilloscope screen in an X-Y format, distinct visual patterns were produced by esophageal, right mainstem bronchial, and normal tracheal intubation. This device, although apparently reliable, is relatively awkward and time-consuming to use.

Visualization of the tracheal rings and carina by fiber optic bronchoscopy is another reliable method of verifying tracheal tube placement. However, the instrument is relatively expensive, prone to breakage, and the method is unwieldy for routine use.

Another technique, pulse oximetry, although useful in many situations, may be a late indicator of esophageal intubation for several reasons. Apparently normal functioning of a ventilator can be observed even when connected to an esophageal tube. This can delay recognition of tube misplacement.

In the operating theater, the most reliable and simple determination of proper tube placement involves capnometry, the measurement of carbon dioxide concentration during the respiratory cycle. The carbon dioxide concentration is displayed as a wave form on a screen which is monitored by the anesthesiologist. The reliability of the carbon dioxide monitoring is based on the assumption of the $CO_2$ can be reliably detected in patients with an intact pulmonary circulation whose trachea is intubated, whereas no $CO_2$ is present in gases exiting from an esophageal tube. In the emergency setting, however, this device is unwieldy and expensive.

Colorimetric end tidal $CO_2$ ($ETCO_2$) is a calorimetric device that is attached to endotracheal tubes to continuously monitor $ETCO_2$ tension. This device is a plastic, disposable unit that enables the user to estimate $ETCO_2$ tension by comparing a calorimetric membrane (that changes color in response to $ETCO_2$ tension) with a calibration color band.

The $ETCO_2$ detector has three color ranges:
A (purple—$ETCO_2$ less than 0.5 percent)
B (tan—$ETCO_2$ 0.5–2 percent)
C (yellow—$ETCO_2$ greater than 2 percent)

Adults with normal hemodynamics and normal respiratory function usually exhale a carbon dioxide tension of approximately 4 to 5 percent. Thus, a correctly placed endotracheal tube should produce a yellow colorimetric signal with the $ETCO_2$ monitor. In patients with cardiac arrest, however, a marked reduction in blood flow, such as that commonly present in closed-chest compression, lowers the $ETCO_2$ reading. Thus, a low value (purple color) can be caused by a number of factors, including: improper endotracheal tube placement, poor blood flow, marked ventilation/ perfusion mismatch (e.g., massive pulmonary embolus), exogenously administered epinephrine, or adequate ventilation. A prolonged period of arrest also appears to be associated with a lower $ETCO_2$ reading.

Other problems associated with the use of $ETCO_2$ to determine tube placement in emergency intubation include high price and limited shelf life. The device also does not provide for real time determination of tube placement. Finally, $ETCO_2$ does not distinguish between correct placement of endotracheal tube, intrabronchial intubation, or endotracheal tube movement into the oropharynx.

Orotracheal intubation using transillumination, which involves introducing a flexible lighted stylet into the trachea, is a well-known technique. Intratracheal placement of the stylet light gives off an intense, circumscribed glow in the region of the laryngeal prominence and the suprasternal notch, indicative of correct tracheal placement of the stylet. An endotracheal tube is then passed over the flexible stylet and secured into the trachea. If esophageal placement occurs, the light is usually not seen, or is perceived as dull and diffuse. Although the lighted stylet is useful under certain circumstances, it does not work well in bright sunlight or in bloody situations, e.g., trauma, and does not provide real time determination of tube placement.

The use of a self-inflating bulb in a suction esophageal detection device to differentiate esophageal from tracheal intubation is based on the principle that the trachea is held open by rigid cartilaginous rings, whereas the esophagus readily collapses when a negative pressure is applied to its lumen. The device works as follows: a self-inflating bulb is connected to the endotracheal tube and the bulb compressed. Refilling of the bulb is instantaneous if the tube is in the trachea. In contrast, if the tube is in the esophagus, compression of the bulb remains collapsed on release of pressure.

Despite the efficiency of the esophageal detector device and the self inflating bulb in differentiating esophageal from tracheal intubation, it may still give false negative results if, for example, the tube is in the trachea, but gas cannot be aspirated by the syringe or the bulb does not reinflate. Furthermore, this suction device also does not provide for real time determination of tube placement and does not distinguish between 1) correct placement of breathing tube in the trachea, 2) breathing tube in the bronchus or 3) breathing tube in the oropharynx.

The possibility of using a nonradiographic, noninvasive technique to determine tracheal tube location was first proposed by Cullen, et al. (*Anesthesiology*, 1975, Vol. 43, pp. 596–599). The method involves an electromagnetic sensing technique to allow the detection of a circumferential foil marker band fused into the endotracheal tube a the proximal cuff tube injunction. A hand-held pocket battery powered detector is utilized to detect the foil marker and locate it with respect to external landmarks of the neck. The detection system, which is based on a differential mutual sensing scheme to measure the distance of the magnetic band placed on the endotracheal tube, is said to allow accurate determination of tube position. Although preclinical trials of a prototype device have been carried out for a pediatric population (McCormick et al., *IEEE/Eighth Annual Conference of the Engineering in Medicine and Biology Society* proceedings, 1986, pp. 140–143), devices of this type have not found wide acceptance in hospitals. This probably reflects the difficulty of detecting a stationary magnetic field.

Mansfield, et al., *IEEE Transactions on Biomedical Engineering*, 1993, Vol. 40, No. 12, pp. 1330–1335) describes an instrument that determines the position of endotracheal tubes by utilizing the acoustical properties of the trachea and bronchus. An incident audible sound pulse is introduced into the proximal endotracheal tube and is detected as it travels down the endotracheal tube via a miniature microphone located in the wall of the tube. This pulse is then emitted from the tube tip into the airways and the reflected signal from the airways is detected by the microphone. A well-defined reflection arises from the point where the total cross sectional area of the airways increases rapidly, and the difference in timing between the detection of the incident pulse and this reflection is used to determine endotracheal tube position or movement. This reflection is not observed if the endotracheal tube is placed in the esophagus. The device, which was tested on dogs, discriminates by cross sectional area between the trachea and the bronchus and insures an adequate fit between the endotracheal tube and the trachea. Tests of this device on humans have not yet been reported. A point of concern is that because this method relies on sound wave generation, it might not prove useful in pulmonary edema, trauma, or in other unforeseeable circumstances.

Endotracheal tubes have been used in association with an ultrasound device. However, they cannot be used to monitor, as in the present invention, the position of the endotracheal tube in a patient, first to confirm that the tube has, in fact, been inserted into the trachea and not into the esophagus, and then to make certain that its tip remains correctly positioned substantially at the midpoint of the trachea for proper ventilation of the patient. Abrams et al., U.S. Pat. No. 4,722,347, and Weber, U.S. Pat. No. 5,076,268, for example, disclose a tracheal probe for determining pulmonary arterial blood flow that includes a tube that extends to the bifurcation, or carina, of the trachea, an ultrasound transducer provided with a lens assembly near the end of the tube, and means for urging the lens assembly against the trachea inner wall. There is no recognition in these references, however, of the possibility and hazards of improper insertion of an endotracheal tube, including esophageal intubation. Furthermore, the apparatus described in these references are incapable of determining the position of an endotracheal tube inserted in a patient.

SUMMARY OF THE INVENTION

The present invention is directed to an endotracheal apparatus for providing reliable airway management in a patient. A flexible tube extends from the patient's oral or nasal cavity to a distal end within the trachea. A first ultrasound transducer means connected to the tube near its distal end is in intimate contact with the forward inner wall of the patient's trachea at substantially its midpoint. A second ultrasound transducer means is disposed in intimate contact with the forward outer skin surface of the patient's neck. Either the first or the second transducer means can be a transmitter of an ultrasound signal provided by ultrasound transducer excitation means, to which it is electrically connected. The other transducer means serves as a receiver, which is connected to ultrasound detector means situated externally to the patient.

Also in accordance with the invention, a process for monitoring the position of an endotracheal tube inserted in a patient utilizes an apparatus comprise a flexible tube extending from the patient's oral or nasal cavity to a distal end and first ultrasound transducer means connected to the tube near its distal end. The process comprises inserting the tube into the patient's trachea to a distance such that the first ultrasound transducer means is disposed substantially at the trachea's midpoint. The first transducer means is placed into intimate contact with the forward inner wall of the trachea at substantially its midpoint, and a second ultrasound transducer means is placed in intimate contact with the forward outer skin surface of the patient's neck at a position at least partially overlying the position of the first transmitter means.

An ultrasound signal is applied to transmitter means comprising either one of the first or second ultrasound transducer means, the other of the transducer means comprising receiver means. The receiver means is monitored for a received ultrasound signal sent from the transmitter means, enabling the position of the endotracheal tube to be determined.

The endotracheal apparatus of the present invention, which may be employed even under bloody trauma conditions, ensures that the endotracheal tube is inserted in its proper position in the trachea and not misdirected into the esophagus. The apparatus furthermore provides for monitoring the endotracheal tube for possible displacement resulting from head/neck movement or transport of the patient.

DETAILED DESCRIPTION OF THE INVENTION

Figure 1:
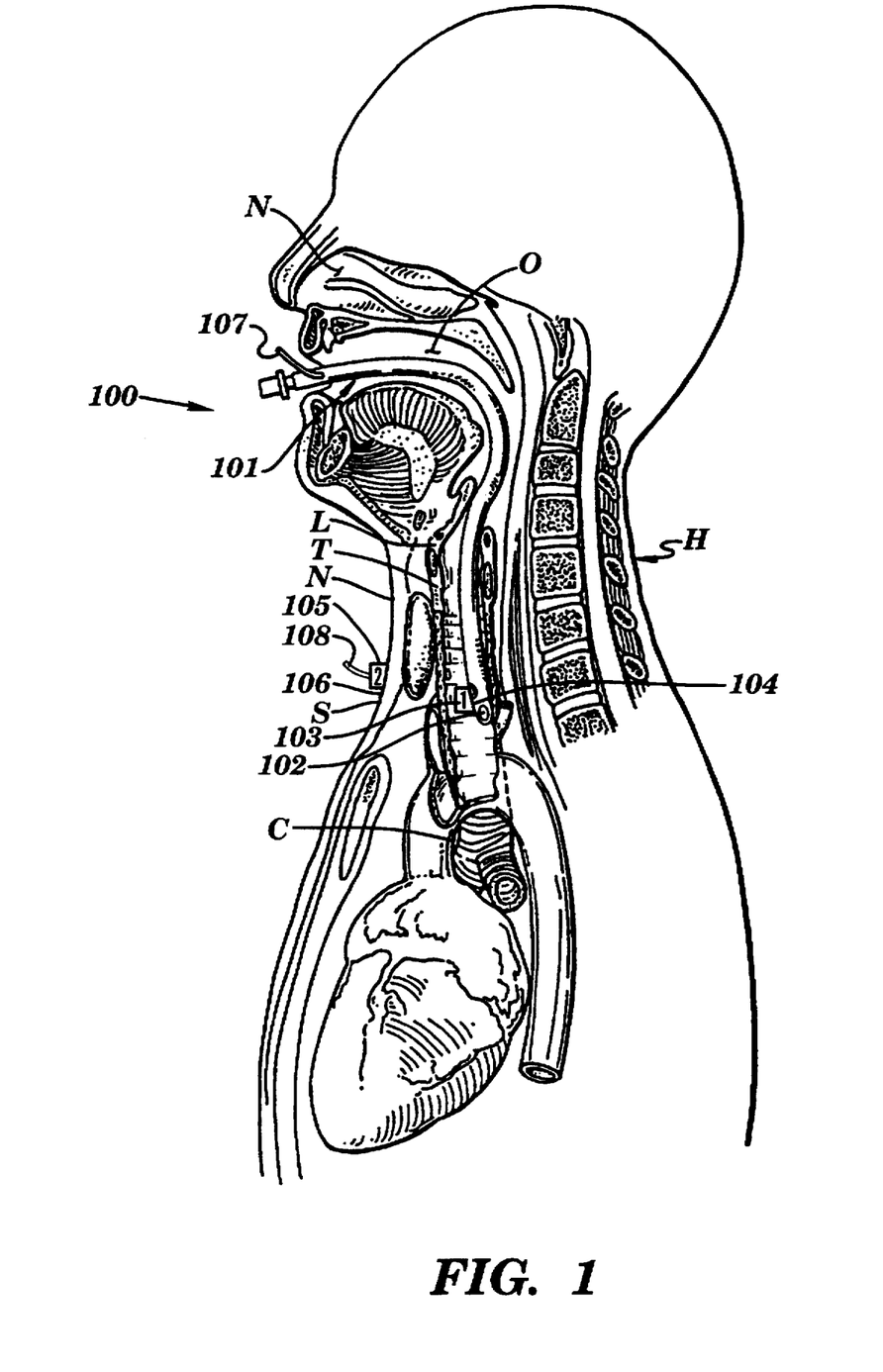
FIG. 1 is a cross-section of a human patient together with a schematic representation of the apparatus of the invention.

FIG. 1 is a sectional view of the upper part of the body of a human H, whose trachea T extends from the larynx L to the carina C, the bifurcation leading to the bronchi (not shown). An endotracheal apparatus 100 is inserted through the oral cavity O, as shown, or through the nasal cavity N into trachea T. Apparatus 100 includes a flexible tube 101 having a distal end 102.

A first ultrasound transducer means 103 is attached to tube 101 near its distal end 102. First transducer means 103 is in intimate contact with the forward inner wall 104 at substantially the midpoint of trachea T. A second ultrasound transducer means 105 is placed in intimate contact with the forward outer skin surface 106 of the neck N in the area above the suprasternal notch S.

In operation, first ultrasound transducer means 103 may be connected by electrical conductor means 107 extending through tube 101 to ultrasound transducer excitation means such as, for example, an electrical pulse generator (not shown), thereby providing transmitter means for sending an ultrasound signal to receiver means comprising second ultrasound transducer means 105, which is connected by electrical conductor means 108 to ultrasound detector means (not shown). Alternatively, second transducer means 105 may be connected to the excitation means and function as the transmitter, first transducer means 103 being connected to the detector means and functioning as the receiver.

Figure 2A:
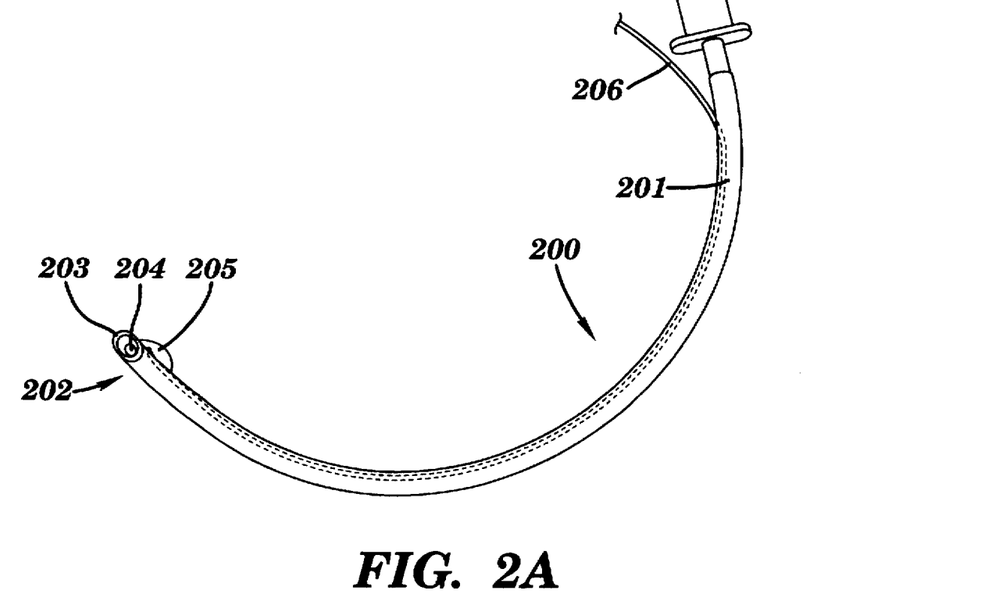
FIGS. 2A and 2B are sectional views of two embodiments of the endotracheal tube of the invention.
Figure 2B:
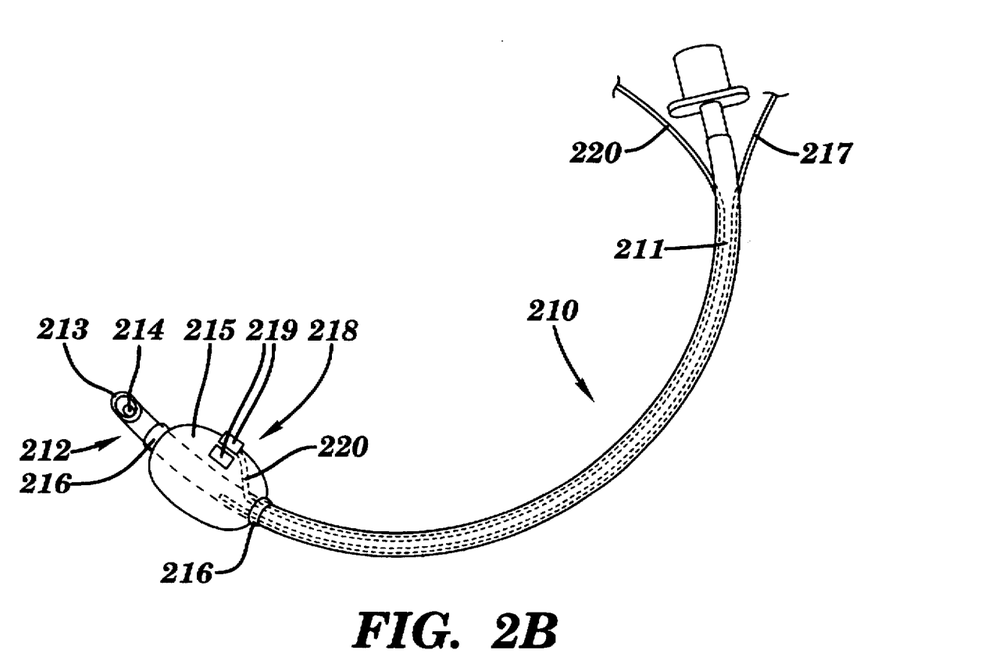

The endotracheal tube apparatus of the present invention comprises embodiments especially useful for pediatric as well as adult patients. FIGS. 2A and 2B depict two such embodiments.

FIG. 2A illustrates an endotracheal apparatus 200 suitable for pediatric patients, typically up to eight years of age, that includes a flexible, preferably plastic, tube 201. The distal end 202 of tube 201 is provided with a standard bevel tip 203 and oppositely directed Murphy eye 204. Also included in apparatus 200 near distal end 202 is ultrasound transducer 205 comprising at least one piezoelectric ultrasound element. In use, transducer 205, which is connected either to transducer excitation means (not shown) or signal detector means (not shown) by electrical conductor 206, is positioned in intimate contact with the forward inner wall of the pediatric patient's trachea at substantially its midpoint.

In accordance with accepted medical practice, endotracheal apparatus 200 intended for pediatric patient use does not include inflatable means such as a balloon. If desired, apparatus 200 may be modified for use with older patients by providing, adjacent to transducer 205, an inflatable balloon cuff (not shown) such as, for example, that described in the aforementioned U.S. Pat. No. 5,076,268, the disclosure of which is incorporated herein by reference.

FIG. 2B depicts a preferred embodiment of the present invention, endotracheal apparatus 210, which is appropriately used with adult patients. Apparatus 210 includes flexible plastic tube 211, whose distal end 212 is provided with bevel tip 213 and Murphy eye 214. Disposed near distal end 212 is inflatable balloon cuff 215, which is secured to tube 211 by a pair of sleeves 216 and inflated through a lumen 217 running along tube 211.

Attached to balloon cuff 215 is ultrasound transducer 218, which comprises at least one and, preferably, a plurality of piezoelectric ultrasound elements 219, at least one of which is urged into intimate contact with the forward inner wall of the patient's trachea at substantially its midpoint by inflation of balloon cuff 215. Piezoelectric elements 219, which may be attached to the inner surface of balloon cuff 215 during its manufacture or subsequently attached to its outer surface, and connected by an electrical conductor 220 running along tube 211 either to transducer excitation means (not shown) or signal detector means (not shown).

In addition to an endotracheal tube provided with a first ultrasound transducer such as the embodiments depicted in FIGS. 2A and 2B, the apparatus of the present invention includes a second ultrasound transducer, also comprising at least one piezoelectric ultrasound element, in intimate contact with the forward outer skin of the patient's neck at a position at least partially overlying that of the first transducer contacting the inner wall of the trachea. The second ultrasound transducer may be affixed to the skin surface by, for example, a material having a self-sticking releasable adhesive surface. When the first transducer is properly positioned in contact with the inner wall of the trachea substantially at its midpoint, and the second transducer is in contact with the outer skin surface of the neck just above the suprasternal notch, an ultrasound signal can be communicated between the two transducers.

Figure 3:
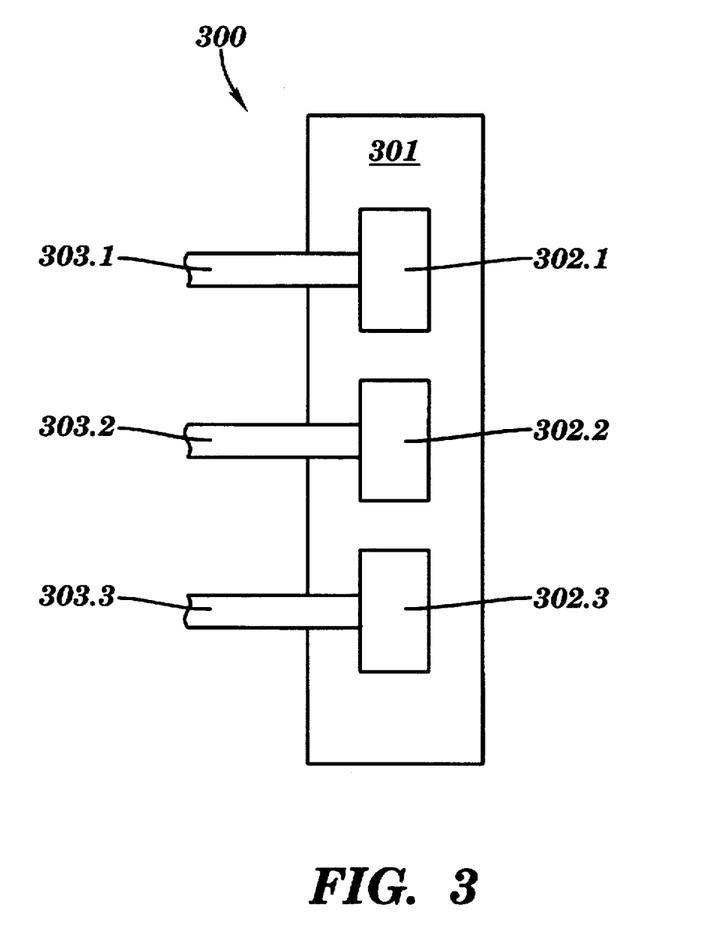
FIG. 3 depicts a device containing second transducer means to be placed on the skin of a patient's neck in accordance with the present invention.

As previously discussed, the second transducer may function, through connection to the excitation means, as a transmitter or, through connection to the detector means, as a receiver. FIG. 3 depicts an embodiment 300 of the second transducer particularly useful as a receiver. Second transducer 300 comprises a releasably adhering strip 301 to which is attached a linear array comprising a plurality of piezoelectric ultrasound elements 302.n, each provided with an electrical conductor 303.n. Electrical conductors 303.n are connected to detector means (not shown), which may be an electronic circuit connecting receiver transducer 300 to signal means (not shown). The array of ultrasound elements is useful for monitoring the position within the patient's trachea of the first transducer attached to the endotracheal tube, e.g., transducer 218 on balloon cuff 215, as shown in FIG. 2B.

The endotracheal apparatus 210 comprising first ultrasound transmitting transducer 218 of FIG. 2B cooperatively functions with the second ultrasound receiving transducer 300 of FIG. 3 to ensure the initial and continued proper positioning of an endotracheal tube within a patient. Elements 219 of transducer 218 and elements 302.n of transducer 300 comprise stacks of piezoelectric films that are designed to be responsive to frequencies between about 1 MHz and 10 MHz. Such elements are commercially available from various sources; for example, a 1-mm-thick stacked element tuned to 2 MHz can be obtained from the AMP Inc., Valley Forge, Pa.

In operation, the apparatus 210 is inserted into a patient, and an ultrasound signal is transmitted from an element 219 of transducer 218 for reception by an element 302.n of transducer 300. Failure of an element 302.n to receive a signal indicates tubal misplacement, in particular, esophageal rather than tracheal insertion of the tube. Such a dangerous situation is immediately detectable by the apparatus of the invention, enabling prompt correction to avoid harm to the patient.

When proper placement of the tube within the trachea is confirmed, the position of transducer 300 can be adjusted on the patient's neck so that the ultrasound signal from an element 219 of transducer 218 within the trachea is received specifically by, for example, the middle element 302.2 of the array of elements 302.n, resulting in appropriate activation of the signal means (not shown). For example, a middle light in an array of display lights corresponding to the array of elements 302.n in transducer 300 may be illuminated. If head/neck movement or transport of the patient causes repositioning of the tube within the trachea, the ultrasound signal from transducer 218 is received by a different element 302.n of the array, causing another light corresponding to the newly activated element to be illuminated. The change in the light display may be accompanied by an audible signal such as a beeper or buzzer, thereby alerting attending personnel to the possible need for repositioning of the tube.

Figure 4:
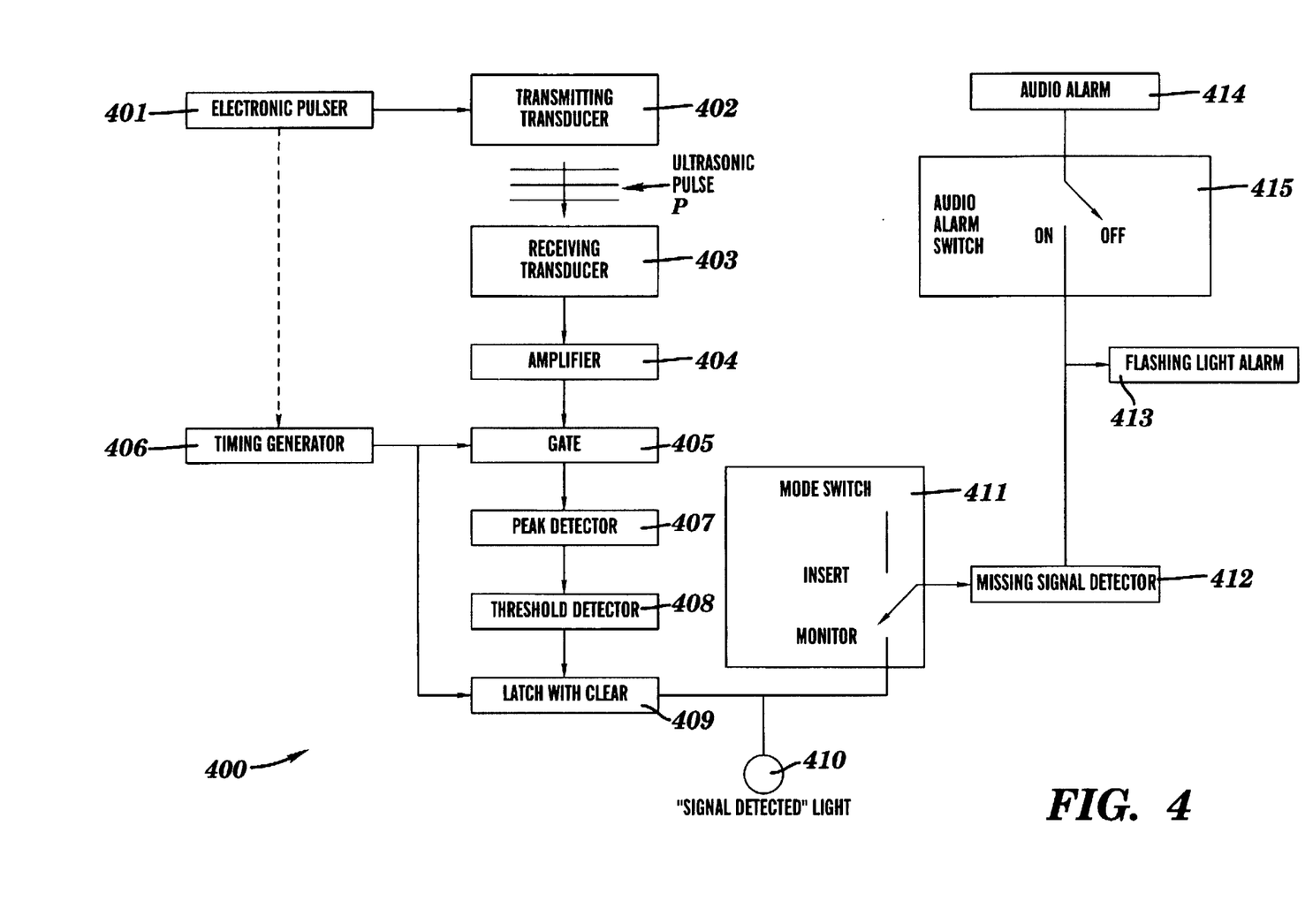
FIG. 4 is a schematic representation of electrical circuitry of the apparatus of the invention.

A preferred embodiment of the electrical circuitry 400 of the apparatus of the invention is represented by a block diagram in FIG. 4. An electronic pulser 401 delivers a high voltage pulse to transmitting transducer 402, which, owing to its thickness and piezoelectric or electrostrictive properties, emits an ultrasonic pulse signal P of a particular frequency, preferably in the 1 to 10 MHz range. This ultrasound signal P travels through the tracheal wall and overlying tissues and skin to a receiving transducer 403, where the mechanical ultrasound signal is converted back to an electrical signal.

This electrical signal is amplified by amplifier 404 and passed through an electronic gate 405, which is driven by a signal from a timing generator 406 that is synchronized to the firing of the electronic pulser 401. This provides a means of rejecting spurious noise signals by only detecting signals that occur at the "correct" time relative to the firing of the transmitter.

The selected signal is then passed to a peak detector 407 to find the maximum signal occurring within the acceptable gate; a threshold detector 408 then determines if the signal exceeds a minimum acceptable level. The output of this stage is a binary value of "1" or "0" corresponding to "Yes, the signal exceeds the threshold" or "No, the signal does not exceed the threshold." A latch 409 then holds that value until reset by the timing generator 406 to accept another value for the next pulse.

As long as the received signal exceeds the threshold value, the "Signal Detected" light 410 remains illuminated. This serves as an indication to the operator that the endotracheal tube is in the trachea and properly positioned. If the "Signal Detected" light 410 does not illuminate, then the endotracheal tube is improperly positioned, either too high or low in the trachea or in the esophagus, and the position should be checked immediately. This portion of the circuit can be modified to service parallel multiple transducers placed on the skin surface to provide information on the positioning of the tube within the trachea, as depicted, for example, in FIG. 3. Thus, for example, if an element 219 of transmitting transducer 218 is closest to element 302.2 of receiving transducer 300, that element will detect the ultrasound signal. The elements 302.n are spaced sufficiently far apart so that only one such element will sense the ultrasound signal. This can be accomplished by adjusting the threshold detector 408 so that it detects an ultrasound signal from only one element 302.n at any given time.

During the initial positioning of the tube, a mode switch 411 is in the "Insert" position, disabling the alarm circuitry following it. Once the operator is satisfied that the tube is properly positioned and the signal is detected, the mode switch 411 is changed to the "Monitor" position, thus connecting the latched signal to a missing signal detector 412 that monitors the level of the signal. If the signal is not detected for one or more pulses of the transmitter, an output signal will go high, activating a flashing light alarm 413 and also an audio alarm 414. The audio alarm 414 can be turned off while the operator finds the cause of the alarm, using audio alarm switch 415. Switch 415 should be capable of re-arming itself after a specified period to prevent it being left off inadvertently.

The invention has been described in detail with particular reference to preferred embodiments thereof, but it will be understood that variations and modifications can be effected within the spirit and scope of the invention.

What is claimed is:

1. An endotracheal tube apparatus for providing reliable airway management in a patient, said apparatus comprising:

flexible tube means extending from a patient's oral or nasal cavity to a distal end disposed within a patient's trachea;

first ultrasound transducer means connected to the flexible tube means in proximity of the distal end thereof and disposed at a position in intimate contact with an anterior inner wall of a patient's trachea at substantially the midpoint of a patient's trachea;

second ultrasound transducer means disposed in intimate contact with an anterior outer skin surface of a patient's neck at a position to transmit an ultrasound signal to or receive an ultrasound signal from said first transducer means within a patient's trachea;

ultrasound transducer excitation means connected by electrical conductor means to transmitter means comprising one of said first and second ultrasound transducer means;

ultrasound detector means disposed externally to the patient and connected by electrical conductor means to receiver means comprising the other of said first and second transducer means; and inflatable means attached to the flexible tube means in proximity to the distal end thereof, wherein the inflatable means comprises the first ultrasound transducer means, said first ultrasound transducer means being urged into intimate contact with an anterior wall of a patient's trachea upon inflating of said inflatable means.

2. The apparatus of claim 1 further comprising:

signal means disposed externally to a patient and responsive to an ultrasound signal received by said receiver means and detected by said detector means, whereby said signal means provides for monitoring the position of the first ultrasound transducer means.

3. The apparatus of claim 2 wherein said signal means comprises visible signal means.

4. The apparatus of claim 3 wherein said visible signal means comprises at least one display light.

5. The apparatus of claim 2 wherein said signal means comprises audible signal means.

6. The apparatus of claim 5 wherein said audible signal means comprises a buzzer or a beeper.

7. The apparatus of claim 1 wherein said second transducer means is held in position on an anterior outer skin surface of a patient's neck by adhering means.

8. The apparatus of claim 7 wherein said adhering means comprises a self-sticking releasable adhesive surface.

9. The apparatus of claim 1 wherein the ultrasound transducer excitation means is disposed externally to a patient.

10. The apparatus of claim 1 wherein said flexible tube means is adapted to provide ventilation of a patient.

11. The apparatus of claim 1 wherein said inflatable means comprises an inflatable balloon cuff.

12. The apparatus of claim 1 wherein said first and second transducer means each comprises a piezoelectric ultrasound element.

13. The apparatus of claim 12 wherein said first transducer means comprises ultrasound signal transmitter means and said second transducer means comprises ultrasound signal receiver means.

14. The apparatus of claim 12 wherein said first transducer means comprises ultrasound signal receiver means and said second transducer means comprises ultrasound signal transmitter means.

15. The apparatus of claim 1 wherein said transducer excitation means comprises an electrical pulse generator.

16. The apparatus of claim 1 wherein said detector means comprises an electronic circuit connecting said receiver means to said signal means.

17. The apparatus of claim 1 wherein said electrical conductor means comprises a conductive wire.

18. The apparatus of claim 1 wherein the second transducer means on an anterior outer skin surface of a patient's neck at least partially overlies the first transducer means on an anterior inner wall of a patient's trachea.

19. A process for monitoring the position of an endotracheal tube inserted in a patient's trachea, said process comprising:

provviding an apparatus comprising a flexible tube extending from a/the patient's oral or nasal cavity to a distal end of said tube, and an inflatable balloon cuff disposed on said tube in proximity of the distal end thereof, said inflatable balloon cuff comprising first ultrasound transducer means;

inserting the flexible tube into a/the patient's trachea to a distance such that the first ultrasound transducer means is disposed within a/the patient's trachea substantially at the midpoint of a/the patient's trachea;

inflating said inflatable balloon cuff, thereby placing said first ultrasound transducer means in a position of intimate contact with an anterior inner wall of a/the patient's trachea at substantially the midpoint of said trachea;

placing second ultrasound transducer means in intimate contact with an anterior outer skin surface of a/the patient's neck at a position at least partially overlying the position of the first ultrasound transducer means in contact with an anterior inner wall of a/the patient's trachea;

applying an ultrasound signal to transmitter means comprising one of said first and second ultrasound transducer means; and monitoring receiver means comprising the other of said first and second ultrasound transducer means for a received ultrasound signal transmitted from said transmitter means, thereby enabling the position of the endotracheal tube to be determined.

20. The process of claim 19 further comprising:

providing signal means responsive to said monitoring.

21. The process of claim 20 wherein said signal means comprises visible signal means.

22. The process of claim 21 wherein said visible signal means comprises at least one display light.

23. The process of claim 20 wherein said signal means comprises audible signal means.

24. The process of claim 23 wherein said audible signal means comprises a buzzer or a beeper.

25. The process of claim 19 wherein said first and second transducer means each comprises a piezoelectric ultrasound element.

26. The process of claim 19 wherein placing the second ultrasound transducer means in intimate contact with an anterior outer skin surface of a/the patient's neck comprises:

releasably attaching said second ultrasound transducer means to an anterior skin surface of a/the patient's neck.

27. The process of claim 19 wherein said ultrasound signal has a frequency of about 1 MHz to 10 MHz.

* * * * *